United States Patent
Phillips et al.

(10) Patent No.: US 9,271,588 B1
(45) Date of Patent: Mar. 1, 2016

(54) PHYSICAL THERAPY COVER

(71) Applicants: Brook D. Phillips, Santa Barbara, CA (US); Sandra Daniel, San Diego, CA (US)

(72) Inventors: Brook D. Phillips, Santa Barbara, CA (US); Sandra Daniel, San Diego, CA (US)

(73) Assignee: EcoPro Products, LLC, Santa Barbara, CA (US)

( * ) Notice: Subject to any disclaimer, the term of this patent is extended or adjusted under 35 U.S.C. 154(b) by 0 days.

(21) Appl. No.: 14/514,092

(22) Filed: Oct. 14, 2014

(51) Int. Cl.
*A47G 9/02* (2006.01)
*A47G 9/04* (2006.01)

(52) U.S. Cl.
CPC ............. *A47G 9/0253* (2013.01); *A47G 9/04* (2013.01)

(58) Field of Classification Search
CPC ............ A47G 2009/001; A47G 9/007; A47G 9/0253; A47G 9/0261; A47G 2400/02; A47G 2400/022
See application file for complete search history.

(56) References Cited

U.S. PATENT DOCUMENTS

| | | | |
|---|---|---|---|
| 4,763,369 A * | 8/1988 | Spector | 5/640 |
| 5,644,807 A * | 7/1997 | Battistella | 5/419 |
| 7,621,005 B1 * | 11/2009 | Harvey | 5/419 |
| 8,347,431 B1 * | 1/2013 | Cohron, III | 5/490 |
| 8,458,832 B1 * | 6/2013 | Krishna | 5/501 |
| 2005/0150048 A1 * | 7/2005 | Hamilton | 5/490 |
| 2007/0056111 A1 * | 3/2007 | Lastman | 5/655 |
| 2007/0261171 A1 * | 11/2007 | Williams et al. | 5/636 |
| 2008/0172792 A1 * | 7/2008 | Dreessen | 5/636 |
| 2008/0235877 A1 * | 10/2008 | Murray et al. | 5/640 |
| 2010/0107336 A1 * | 5/2010 | Ross | 5/490 |
| 2011/0023235 A1 * | 2/2011 | Gold | 5/501 |
| 2012/0066837 A1 * | 3/2012 | Thorsen et al. | 5/657 |
| 2012/0144590 A1 * | 6/2012 | Sharp | 5/639 |
| 2012/0289116 A1 * | 11/2012 | Beuerle | 446/72 |
| 2013/0042410 A1 * | 2/2013 | Bice | 5/490 |
| 2013/0091629 A1 * | 4/2013 | Eaton et al. | 5/490 |
| 2013/0119716 A1 * | 5/2013 | Stronconi | 297/180.1 |
| 2013/0125435 A1 * | 5/2013 | Keever | 40/620 |
| 2013/0183495 A1 * | 7/2013 | Rock | 428/156 |
| 2013/0227784 A1 * | 9/2013 | Holliday et al. | 5/490 |
| 2013/0312192 A1 * | 11/2013 | Lee | 5/639 |
| 2014/0109318 A1 * | 4/2014 | Loos | 5/644 |
| 2014/0196214 A1 * | 7/2014 | DuPre | 5/644 |
| 2014/0256216 A1 * | 9/2014 | Gordinho | 446/369 |
| 2014/0283303 A1 * | 9/2014 | Rochlin | 5/636 |

\* cited by examiner

*Primary Examiner* — David E Sosnowski
(74) *Attorney, Agent, or Firm* — Mary M. H. Eliason

(57) ABSTRACT

The present disclosure is directed to a physical therapy pillow cover including: a cover made of antimicrobial water resistant fabric, one or more seams, an opening, and a loop strap.

13 Claims, 2 Drawing Sheets

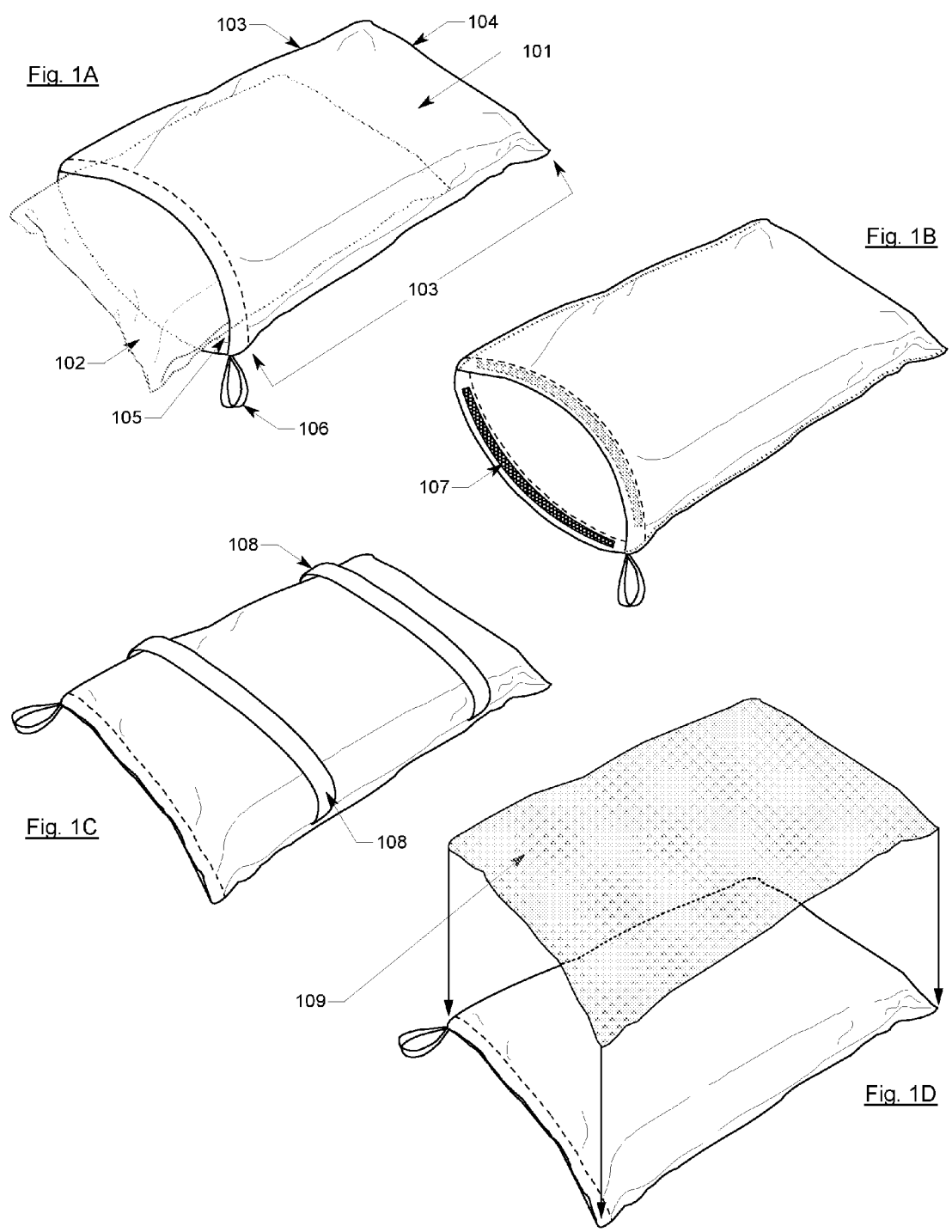

PHYSICAL THERAPY COVER

BACKGROUND OF THE INVENTION

A physical therapy clinic is a fast-paced and physically demanding environment. There are competing pressures to see ever more patients, while providing superior physical care, in a clean environment, while limiting the amount of trash and/or use of environmentally harmful cleaning agents.

Thus, the interests of patient comfort, patient safety and treatment compete with the realities of an increased number of patients per therapist, and the consequent increased number of disposable sheets, pillows, or other medical supplies have created both stresses on patient comfort and cost to the clinic. Moreover, even if disposable materials are not used, the cleaning requirements needed to maintain a safe and clean environment for the significant number of patients leads to an extensive use of laundering using large amounts of water and detergents.

Finally, due to the physical demands unique to the physical therapy clinic, any supplies used therein need to be easily storable and retrievable, quickly cleanable, resistant to physical stresses, and enhance patient comfort during manipulations of the patient during treatment.

The present covers provide a specific solution to address the particular needs of the physical therapy environment.

BRIEF SUMMARY OF THE INVENTION

The present invention is directed to a physical therapy pillow cover comprising: a cover made of antimicrobial water resistant fabric, one or more seams, an opening, and a loop strap. In another embodiment, the cover is also resistant to physical stress.

In one embodiment the physical therapy pillow cover includes a closure device for securing the opening. In an aspect of this embodiment wherein the closure device is a zipper, one or more buttons or snaps, hook-and-loop closures, Velcro, or holes and lacings. In one embodiment, the closure is a zipper covered by a flap of fabric.

In one embodiment the fabric is selected from the group consisting of: vinyl, polyurethane, PVC-coated polyester, polyurethane backed with a polyester/cotton blend, silicone elastomer-coated fabrics, fluoropolymer-coated fabrics, CRYPTON®-treated fabrics, silver ion coated or embedded fabrics.

In yet another embodiment, the physical therapy pillow cover comprises one or more additional straps. In an aspect of this embodiment, the strap is made of fabric, rope, polyester, leather, nylon, hemp, or cotton. The strap may be the same fabric as the pillow cover or a different fabric from the pillow cover.

In yet another aspect the strap is a loop that may be opened, and comprises a buckle, Velcro, or one or more snaps.

In a further embodiment, the pillow has two straps, the first strap is adhered to the center of a side of the pillow, and the second strap is looped through the first strap.

BRIEF DESCRIPTION OF THE SEVERAL VIEWS OF THE DRAWING

FIG. 1A: The physical therapy pillow cover (101) covers the pillow (102). In one embodiment the pillow cover has two long seams (103), and two short seams (104). The pillow cover has an opening (105), and a strap or loop (106).

FIG. 1B: In an additional embodiment, the physical therapy pillow cover may have a closure (107), such as a Velcro closure to keep the opening closed.

FIG. 1C: In yet another embodiment, the physical therapy pillow cover may have one or more additional straps (108).

FIG. 1D: In yet another embodiment, one or more sides of the pillow may be coated with a textured surface (109), which may be layered on, printed on, or screened onto the surface of the pillow cover.

DETAILED DESCRIPTION OF THE INVENTION

Figure 2A:
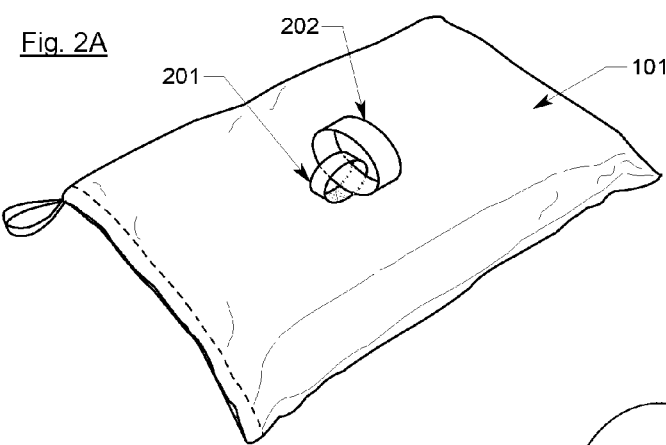
FIG. 2A: A short strap (201) is stitched to the center of the flat side of the pillow cover (101). A second loop (202) is threaded through the first loop.
Figure 2B:
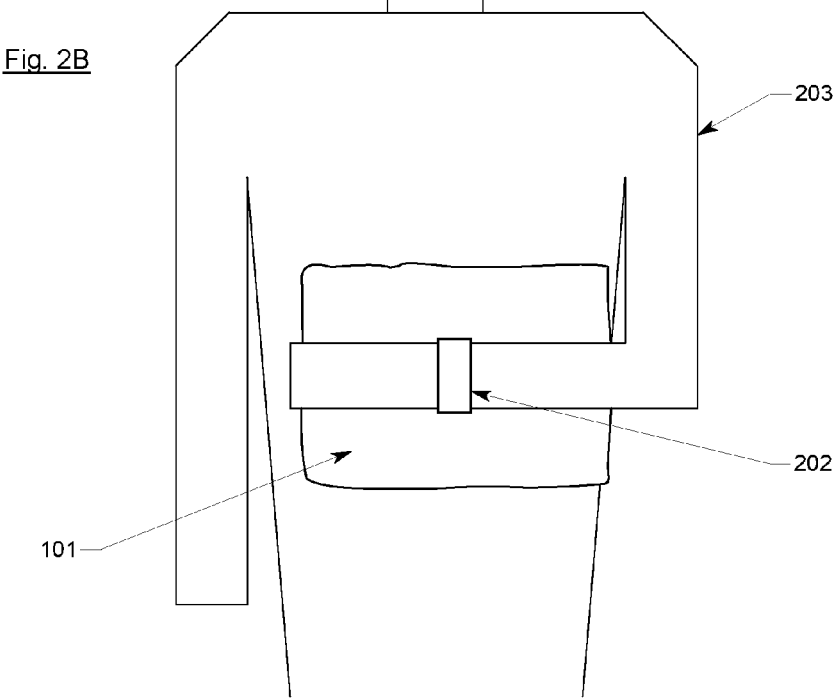
FIG. 2B: The second loop is threaded through the first loop such that it easily fits over the wrist/lower arm of the therapist or patient (203).

The present disclosure is directed to a cover for a physical therapy pillow or support which is made of antimicrobial water resistant fabric, and has an opening, and a loop strap.

The pillow used inside the cover can be a conventional pillow such as one used for head support on a bed, having any conventional filling, including down, polyfill, polyester, beans, buckwheat hulls, latex, foam, gel etc. The pillow may be very compressible or only somewhat compressible depending on the use it is applied to.

Pillows in physical therapy are used as supports and as active devices in the treatment of patients. For instance, a pillow can help maintain the conformation of an injured limb or body part while the limb is being treated by physical manipulation from the therapist, or during other types of treatment such as ultrasound, electrostimulation, ice or heat treatment, or infra-red treatment. The pillow in physical therapy may also actively be used as part of the treatment as a cushion between the therapist and the patient, as the therapist applies body weight to adjust the patient's injured body part (such as shoulders, backs, hips, legs etc.).

The pillow when not in active use should be storable. In one embodiment the cover is storable by hanging. In aspect of this embodiment, the pillow cover includes a strap or loop on its interior or exterior surface which allows it to hang from a hook or peg. If the strap is attached to the exterior surface it may be attached to any portion of the pillow cover, including a "flat" surface side of the cover, at a seam of the pillow cover, at a corner of the pillow cover, or attached to the closure mechanism of the pillow cover. If the strap is attached to the interior surface, the strap may be attached to the "flat" surface side of the cover, a seam of the cover, or the closure mechanism. It would be expected that the strap extend through the opening of the cover to the outside, such that the pillow and cover may be hung without turning the cover inside-out. The strap material is not limited and may be made of fabric, rope, polyester, leather, nylon, hemp, or cotton. The strap may be adhered to the pillow cover by any conventional means, such as glue, stitching, snap, or buckle. In one embodiment the strap is an extension of the pillow cover fabric shaped into a strap form.

The location and size of the strap or loop may be determined based on its use. In one embodiment, the strap or loop is at least 2, at least 3, at least 4, at least 5, at least six, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, or at least 40 inches in length.

In one embodiment, there may be multiple straps or loops. In one embodiment, the multiple straps are oriented at opposite sides of the cover such that the pillow cover may be adhered to a surface or table. In an aspect of this embodiment, the straps may be tied around a surface or table to prevent movement of the pillow and cover during physical therapy manipulations or exercises. In another aspect, the multiple straps may be tied together around an object.

In a further embodiment, the strap is structured so that it ends in a loop and thus is a combined strap and loop. The loop may have further attachment devices attached to it, such as carabiners, snaps, etc.

In one embodiment, the strap or loop is able to be opened, such that it becomes a linear strap when opened, and a loop when closed. In an aspect of this embodiment, the strap/loop may include a closure mechanism, such as Velcro, snaps, hooks, male/female plastic connectors, slide release or cam buckles, rings, slides etc.

In one embodiment, the cover is reversible. That is, the inside and outside surfaces of the cover may both be used in the physical therapy context. In one embodiment, the interior and exterior surface of the cover are substantially identical. By substantially identical it is meant that the surfaces of the fabric have similar qualities in their resistance to water, texture of the surface, or "feel." The seams may or may not be similar, and in one embodiment of the reversible cover, the seams are encased in fabric.

In one embodiment, the pillow is storable by stacking, and incorporates a textured surface which prevents sliding when stacked against other pillows, paper, sheets, towels, tables or other structures. The textured surface may be an additional coating on the outside of the pillow cover, an additional layer, or may be a feature of the fabric of the pillow cover. The textured surface may cover the entirety of the pillow, one side of the pillow (so that the patient's head contacts the untextured surface), or one portion of one or more sides of the pillow. The textured surface may be a non-slip treatment, rubberized, latex, plasticized, PVC treated or coated, vinyl treated or coated, or neoprene coated. The texturing may be in a regular pattern, a decorative pattern, or a logo, covering an adequate surface to prevent slippage of the pillow cover against an exterior surface. The textured surface may be an intrinsic property of the material of the pillow cover, sprayed on, printed on, sewn on, laminated, glued, or otherwise adhered to the pillow cover.

The pillows within the scope of the present embodiments are durable. The pillow covers in particular have a high tensile strength, high tear resistance, and resistant to physical stresses, such as shear, wear, or fraying. In one embodiment the fabric is water resistant. In one embodiment the fabric is antimicrobial or antibacterial. In addition, the fabric may be anti-static. In one embodiment, the fabric is one or more layers of vinyl, polyurethane, PVC-coated polyester, polyurethane backed with a polyester/cotton blend, silicone elastomer-coated fabrics, fluoropolymer-coated fabrics, CRYPTON®-treated fabrics, or silver ion coated or embedded fabrics. A fabric may be "backed" with a second fabric material or fibers. In one aspect the backing is adhered to the exterior fabric by glue or adhesive, stitched to the interior surface of the pillow cover at the seams, quilted, or interwoven with the exterior fabric.

In one embodiment the fabric is free of environmental contaminants. In one embodiment, the fabric is PVC free. In one embodiment, the fabric is a natural fabric which may or may not be treated for water resistance.

The shape of the pillow cover is not particularly limited. For instance it may be square, rectangular, horse-shoe shaped, cylindrical, pyramidal, triangular, or even spherical. The shape will be determined by the use to which it is put. For instance, if the pillow is intended to support the head and neck when the patient is on his or her back, then it may be roughly rectangular (as in a bed pillow), cylindrical (to support the neck), the shape of a European-style pillow (roughly square with an approximately flat upper and lower surface), suspension bridge shaped (e.g. two high peaks with a parabola shaped indentation between the two peaks, for stabilization of the neck or other body part). In an example where the patient is receiving therapy while face-down, the pillow and corresponding pillow cover may be horse shoe shaped to contact the forehead, temples and cheeks of the patient.

The size of the pillow cover is also not particularly limited and may either closely or loosely follow the contours of the pillow. For instance if the pillow is a standard 20×26" pillow then the pillow cover may be 21"×32" (pillow sizes are typically standard: 20×26"; queen: 20"×30"; king: 20"×6"; European Square: 26"×26" etc.) Thus, there is about an inch of space for each seam. In one embodiment the cover is sized to be at least about one inch longer than each dimension of the pillow, at least about 1.5" longer than each dimension of the pillow, at least about 2" longer than a dimension of the pillow; at least about 2.5" longer than a dimension of the pillow; at least 3" longer than a dimension of the pillow; at least 3.5" longer than a dimension of the pillow; at least 4" longer than a dimension of the pillow; at least 4.5" longer than a dimension of the pillow; at least 5" longer than a dimension of the pillow; at least 5.5" longer than a dimension of the pillow; at least 6" longer than a dimension of the pillow; at least 6.5" longer than a dimension of the pillow; at least 7" longer than a dimension of the pillow; at least 7.5" longer than a dimension of the pillow; or at least 8" longer than a dimension of the pillow.

There may be more space given in the cover size to one particular dimension as opposed to another dimension of the pillow.

The pillow cover may be open at one or more seams, have a closure or may fully and permanently enclose the pillow. In one embodiment, the cover is open at one seam, permitting the replacement of the pillow. In another embodiment, the pillow cover has one or more closures. The type of closure is not particularly limited, and may be a zipper, Velcro, "zip lock," snaps, hooks, buckles, or laces etc. The closure may cover the entire seam or may allow openings. If fully covering the entire seam, it should allow passage of air between the interior of the cover to the exterior and vice versa, as air will need to escape if the pillow is compressed. The closure may be hidden by a flap of fabric of the cover or apparent. It is preferred that the closure not be in contact with the patient when the pillow cover and pillow is in use.

The invention will now be described in non-limiting examples, which the skilled artisan will notice may be varied.

EXAMPLES

1. Physical Therapy Loop Pillow Cover

In one embodiment, the pillow cover is made of a backed fabric, where the fabric is a PVC free vinyl, and the fabric is backed with a polyester grid. In one corner a woven polyester strap having a one inch width and a 10 inch length (encompassing the whole of the loop) is sewn into the seam. The pillow cover is 22×36". The closure is a zipper attached to the short side of the cover and covered by a flap of fabric. The pillow and pillow cover are used to support a patient's head or limb. The pillow is cleaned after every use by a patient with a anti-microbial cleanser. The pillow cover is resistant to blood, mucous, sweat, tears, or other bodily fluids. The pillow cover after 30 plus cleanings does not show wear.

2. Physical Therapy Manipulation Pillow Cover

In another embodiment, the pillow is 9"×13" and roughly rectangular in shape. A short (3") nylon strap is stitched to the center of the flat side of the pillow cover (e.g., the top). A second loop is threaded through the first loop and is about 12 inches in length, such that it easily fits over the wrist/lower arm of the therapist or patient. The second loop is a stabilizing loop used to position the pillow between the physical therapist and the patient for "hands on" manipulations to adjust the back and shoulders of the patient. The therapist places the pillow either on his arm or the arm of the patient. The patient lays on their back and crosses their arms over their chest with the pillow being placed between the patient and the therapist. The therapist then leans over the patient's torso, and applies force to the patient's arms and/or shoulders. The pillow cover protects both the therapist and the patient from bruising. The pillow cover may be stored by hanging on a hook, and cleaned for use with subsequent patients.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A physical therapy pillow cover system comprising:
a generally rectangular physical therapy pillow cover made of antimicrobial water resistant fabric, one or more seams, an opening, and a plurality of loop straps; wherein a first loop strap of the plurality of loop straps is stitched to the center of a flat side of the pillow cover, the first loop strap being about three inches in length; wherein a second loop strap of the plurality of loop straps is threaded through the first loop strap, is about 12 inches in length, and is configured to easily fit over a wrist or arm of a physical therapist or a patient so as to stabilize and position the pillow between the physical therapist and the patient to protect both the therapist and the patient from bruising during an application of force to the patient's arms and/or shoulders.

2. The physical therapy pillow cover of claim 1, further comprising a closure device for securing the opening.

3. The physical therapy pillow cover of claim 1, wherein the cover is configured to be resistant to tearing, and physical stresses including shear, wear, and fraying.

4. The physical therapy pillow cover of claim 2, wherein the closure device is a zipper, one or more buttons or snaps, hook-and-loop closures, or holes and lacings.

5. The physical therapy pillow cover of claim 1, wherein the fabric is selected from the group consisting of: vinyl, polyurethane, PVC-coated polyester, polyurethane backed with a polyester/cotton blend, silicone elastomer-coated fabrics, fluoropolymer-coated fabrics, and silver ion coated or embedded fabrics.

6. The physical therapy pillow cover of claim 1, further comprising one or more additional straps attached to a corner of the pillow cover.

7. The physical therapy pillow cover of claim 1, wherein the straps are made of fabric, rope, polyester, leather, nylon, hemp, or cotton.

8. The physical therapy pillow cover of claim 7, wherein the straps are fabric and wherein the fabric is the same fabric as the pillow cover or a different fabric from the pillow cover.

9. The physical therapy pillow cover of claim 7, wherein the strap is a loop that may be opened, and comprises a buckle, or one or more snaps.

10. The physical therapy pillow cover of claim 1, wherein the pillow cover further comprises a textured, non slip surface covering at least one portion of a flat surface side of the pillow cover.

11. The physical therapy pillow cover of claim 10, wherein the textured surface is layered on, printed on, or screened on the flat surface side of the pillow cover.

12. The physical therapy pillow cover of claim 2, wherein the closure device covers the entire opening, but allows passage of air through the opening.

13. The physical therapy pillow cover of claim 2, wherein the closure covers a portion of the opening, but allows passage of air through the opening.

* * * * *